United States Patent [19]

Krauter et al.

[11] Patent Number: 4,649,904
[45] Date of Patent: Mar. 17, 1987

[54] BIOPSY SEAL

[75] Inventors: Allan I. Krauter, Syracuse; Fred C. Cope; John H. Bean, both of Skaneateles Falls, all of N.Y.

[73] Assignee: Welch Allyn, Inc., Skaneateles Falls, N.Y.

[21] Appl. No.: 815,724

[22] Filed: Jan. 2, 1986

[51] Int. Cl.⁴ .............................................. A61B 1/00
[52] U.S. Cl. ...................................... 128/6; 604/167; 285/331
[58] Field of Search ........................................ 128/4-8; 604/167, 241-243, 283; 285/331

[56] References Cited

U.S. PATENT DOCUMENTS

| 3,512,806 | 5/1970 | Romney et al. | 604/242 X |
| 4,000,739 | 1/1977 | Stevens | 604/169 X |
| 4,240,411 | 12/1980 | Hosono | 128/6 X |
| 4,263,897 | 4/1981 | Terayama | 128/7 |
| 4,424,833 | 1/1984 | Spector et al. | 604/167 X |
| 4,452,473 | 6/1984 | Ruschke | 604/283 X |

Primary Examiner—Dalton L. Truluck
Attorney, Agent, or Firm—Bruns and Wall

[57] ABSTRACT

A disposable seal is provided for a luer lock end fitting, e.g. for a biopsy channel of an endoscope. The fitting has a tubular luer lock device and a retaining ring surrounding the tubular device. The seal is unitarily molded of a soft elastomer and has a double seal arrangement formed of an apertured end wall and a one-way-opening slitted plate or web behind the end wall. A distal end of the seal fits over the tubular luer lock device. This distal end has a radial cuff that seals against a flat transverse surface of the retaining ring and a frustoconic tapered protruding member which fits against a similar inner surface of the retaining ring to ensure that the cuff sealably engages the retaining ring under overpressure conditions.

20 Claims, 5 Drawing Figures

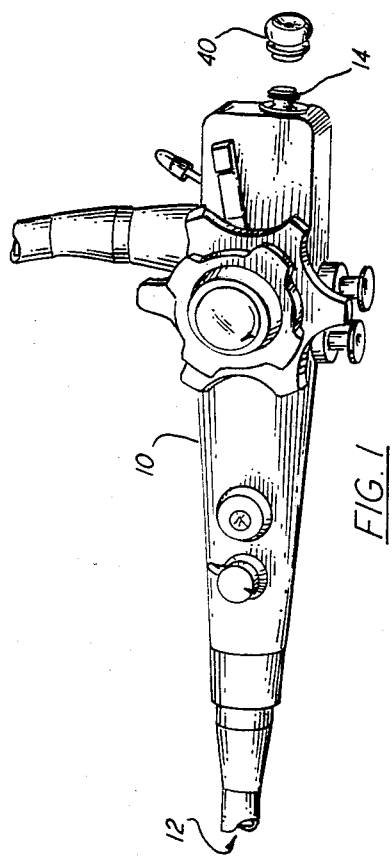
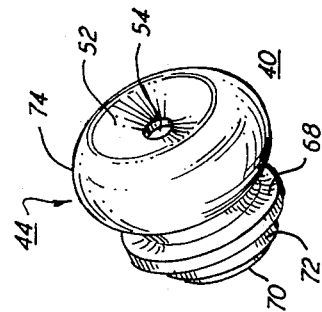
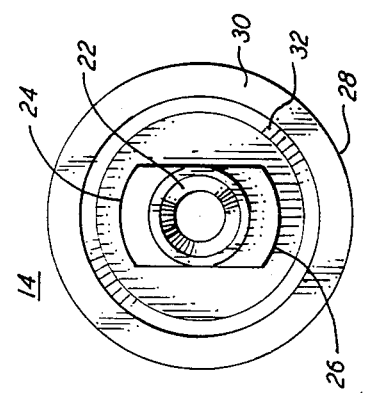
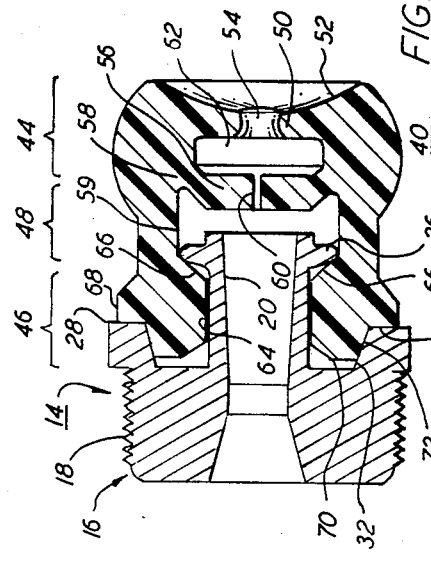
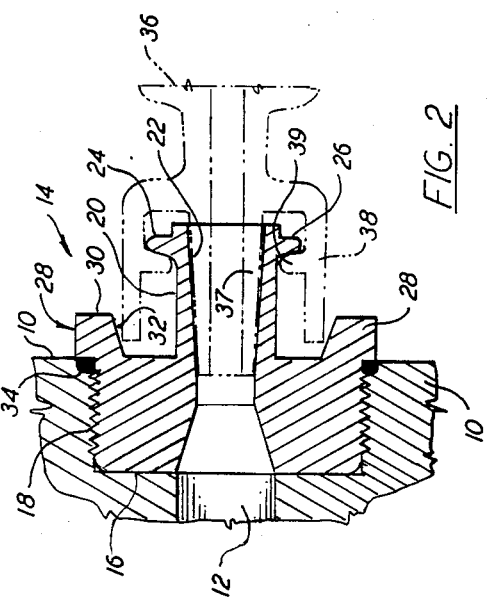

BIOPSY SEALW

BACKGROUND OF THE INVENTION

This invention relates to sealing devices, and is more particularly directed to disposable entrance seals to be used on an external opening of a biopsy channel, the latter typically being included in a medical endoscope.

Current biopsy seals are typically formed of a two-part metal holder and a pair of slitted membranes held in the holder. The slits of the membranes are disposed crosswise to each other and the holder, being threaded, is screwed into a receptacle in the external side of an endoscope biopsy channel.

When it is desired to take a tissue sample, an elongated forceps, with a loop or claw at its distal end, is inserted through the crossed slits into the channel and after obtaining the tissue sample is extracted through the channel and out through the slits of the seal.

The forceps or other instrument is of round external cross-section, but the crossed slits, once penetrated, do not assume a circular shape. Pulsing of fluid pressures in the biopsy channel can cause leakage, and in some cases squirting, of a patient's body fluids out of the seal. This can present hygienic problems to the attending physicians and other medical personnel, especially if the patient being examined has a contagious condition.

The typical seal as described above is not disposable, and must be taken apart and cleaned between uses. This adds to the difficulty of carrying out an endoscopic diagnosis and adds significantly to the cost of examination.

Also, in a typical endoscope, the external entrance to a biopsy channel has no provision for convenient attachment of usual, standard medical devices, thus increasing the difficulty of necessary steps, such as the injection of normal saline solution or water into the biopsy channel, or the sampling of body fluids by withdrawing them into a syringe. For this purpose, a standard luer lock fitting should be provided at the biopsy channel entrance, but no such fitting has been employed at the entrance.

Previously proposed disposable biopsy channel entrance seals do not ensure good seals against insertion of a medical instrument, and the entrance to the channel does not provide for attachment of a typical syringe, as it will not attach to a standard luer lock fitting.

OBJECTS AND SUMMARY OF THE INVENTION

It is an object of this invention to provide a biopsy channel entrance device and sealing arrangement that avoid the problems of the prior art.

It is a particular object of this invention to provide a disposable entrance seal which securely closes the biopsy channel when an elongated medical instrument has been inserted therethrough, as well as when no such instrument has been inserted.

It is another object of this invention to provide a disposable entrance seal which can be easily applied and removed by finger and without tools.

It is still another object of this invention to provide a seal which will sealably accommodate forceps having diameters over a rather broad range.

It is yet another object of this invention to provide a biopsy channel entrance which will seat the disposable seal and which will also accommodate syringes or other devices that have a standard luer lock fitting.

In accordance with an aspect of this invention, the entrance or external end of the biopsy channel of an endoscope (or like device) is provided with an entrance fitting that will accommodate the seal of this invention that is especially adapted for seating thereon.

The entrance fitting is a metal plug having an axial tapered bore, with a hollow luer stem disposed axially on the plug on the external or proximal side. The stem has a pair of oppositely disposed radial flanges at its proximal or free end. A retaining ring is formed on the proximal side of the plug, and this ring has a flat transverse surface and a tapered inner surface facing the stem. This luer lock fitting will admit insertion of the elongated forceps or other instrument, will seat the disposable seal, and will also fit a syringe or any other medical device having a mating standard luer lock fitting.

The disposable biopsy channel entrance seals are formed of an elastomeric biocompatible synthetic resin, and are attached to the above fitting by snapping the seal onto the fitting and rotating the seal a fraction of a turn. The seal is formed of a generally tubular body having a distal seating portion that sealably seats onto the stem and retaining ring, a proximal sealing portion that seals the channel both when the forceps has been inserted and when not, and a medial portion joining the two other portions.

The proximal sealing portion has an outer transverse wall with a central circular opening and a slitted sealing web or plate that is hinged so as to open only in the distal direction. The transverse wall and sealing plate define a disc-like cavity between them, which is favorably factory-filled with a lubricant or sealing grease. The distal seating portion has a radial flange that seals against the transverse flat surface of the sealing ring of the fitting, and a distally protruding annulus with a tapered outer surface to mate with the inner surface of the sealing ring.

The slitted sealing plate seals the biopsy channel until a forceps is inserted, at which time the circular aperture in the proximal sealing wall seals against the circular wall of the forceps. The forceps can have a diameter from about 2.2 mm up to about 3.8 mm. The lubricant in the cavity between the sealing wall and plate facilitates the passage of biopsy forceps or other tools. The distal seating end of the disposable seal mates with the stem and ring of the fitting, ensuring a good seal, even under positive pressure in the biopsy channel. Any overpressure in the channel urges the tapered protruding annulus against the retaining ring, and this distorts the elastomeric seal so as to maintain the force of the sealing flange onto the transverse surface of the retaining ring, so that pulses of pressure will not result in leakage of fluids out the seal.

The above and many other objects, features, and advantages of this invention will become more apparent from the ensuing description of a preferred embodiment, given by way of example and not for limitation, which description should be considered in connection with the accompanying drawing.

BRIEF DESCRIPTION OF THE DRAWING

FIG. 1 is a perspective view of an endoscope controller employing the fitting and seal of this invention;

FIG. 2 is a section view of a luer lock type fitting according to one embodiment of this invention;

FIG. 3 is an axial plan view of the fitting of FIG. 2;

FIG. 4 is a section view of the fitting of FIG. 2 and an associated seal according to an embodiment of the invention; and FIG. 5 is a perspective view of the seal of FIG. 4.

DETAILED DESCRIPTION OF THE PREFERRED EMBODIMENT

With reference to the drawings, and initially to FIGS. 1, 2 and 3 thereof, a control 10 for an endoscope having a biopsy channel 12, has an end fitting 14 formed of a generally cylindrical plug 16 having threads 18 which fit mating threads of the endoscope control 10. The plug 16 has a luer stem 20, of standard construction, the stem 20 having a tapered bore 22 extending through the stem and continuing axially through the plug 16 to communicate with the biopsy channel 12. The stem 20 extends proximally, i.e. to the right in the drawing or away from the channel 12, and has a pair of projecting flanges 24 and 26 which extend radially on opposite sides of the proximal or free end of the stem 20.

A retaining ring 28, here constructed as an integral annular flange surrounds the stem 20 and has a transverse flat surface 30 and a tapered frustoconic inner surface 32 that faces the stem 20. An O-ring 34 is disposed between the threads 18 and the retaining ring 28 and seals the plug 16 of the fitting 14 to the endoscope control 10.

Also shown in FIG. 2 is a syringe 36 (here represented in ghost lines) having a standard luer lock fitting that meets with the end fitting 14. For this reason, an inner hollow male projection 37 fits into the tapered bore 22 of the stem 20 and an outer tube 38 surrounds the projection 37 and contains threads or projections 39 which engage the flanges 24 and 26 by twisting of the syringe 36. Here, the clearance between the retaining ring 28 and the luer stem 20 is sufficient to accommodate this outer tube 38. The syringe 36 can be easily coupled to the biopsy channel 12 by means of the luer stem 20 to blow out the biopsy channel 12, e.g. with water or normal saline solution, when the channel 12 has become clogged during a medical procedure.

The fitting 14, with the exception of the O-ring 34, is unitarily formed of a single block of stainless steel.

As illustrated in FIGS. 4 and 5, a seal 40 according to one embodiment of this invention is adapted for sealably seating onto the luer stem 20 of the end fitting 14 of FIGS. 2 and 3. This seal 40 is formed of a body of a biocompatible soft elastomeric material and has a proximal end portion 44, a distal end portion 46, and a medial portion 48 connecting the portions 44 and 46. The proximal end portion 44 is formed of a front or proximal wall 50, here having a concave spherical surface 52 with a circular sealing opening 54 disposed at the center thereof. Behind this front wall 50 is a web or plate 56 connected by a hinge portion 58 to a generally tubular side wall 59. The plate 56 has a slit 60 therethrough extending across the plate 56 in one direction.

The front wall 50 and the hinged slitted plate 56 together define a generally disc-shaped cavity 62 therebetween.

The distal end portion 46 of the seal 40 has a generally cylindrical inner surface 64 which fits onto the stem 20 of the fitting 14, this surface 64 having a shoulder 66 at its proximal end for engaging beneath the flanges 24 and 26 of the fitting 14. A sealing cuff 68 extends radially outward and engages the flat transverse surface 30 of the retaining ring 28. A protruding annulus 70 extends distally of the cuff 68 and has a tapered frustoconic outer surface 72 which mates with the surface 32 of the retaining ring 28.

As is also apparent from the drawings, the proximal end portion 44 of the seal 40 has a generally barrel-shaped outer surface 74, and the medial portion 48 of the seal is thinner walled than the other portions 44 and 46.

The hinge 58 and plate 56, constructed generally as shown here, admit one-way opening of the slit 60, i.e., so that pressure from the proximal side of the plate 56 will open the slit 60, but pressure applied to the distal side of the plate 56 will urge the slit 60 to be more tightly closed. To accomplish this, the hinge 58 is formed somewhat undercut at the distal side of the plate 56, with the hinge portion 58 extending here diagonally to the side wall 59 at an angle of about 45 degrees and proximally towards the wall. Thus, the slit 60 will open when a forceps or other tool is inserted into the seal, but will not yield to pressure from body fluids which may be conveyed up through the biopsy channel 12. It should also be noted that the circular opening 54 on the front wall seals on the circular outer wall of the instrument, such as the forceps, loop, etc., of the type having a circular cross-section sleeve. The opening 54 in this embodiment is of about 0.065 inches in diameter, and will accommodate instruments ranging in size from 2.2 mm to 3.8 mm.

In this embodiment, the disc-shaped void 62 is factory-filled with a suitable biocompatable grease or lubricant to facilitate the insertion and removal of the medical instrument through the circular opening 54 and the slit 60.

The cuff 68 forms a seal with the flat surface 30 of the retaining ring 28, with the protruding annulus 70 fitting snugly against the frustoconic inner surface 32 of the ring 28. An internal pressure acting on the seal 40 will deform the same so as to bias the annulus 70 against the inner surface 32 of the ring 28 so that good sealing is ensured even in the presence of an internal overpressure. In this embodiment, the taper of the surface 32 and the surface 72 are about 12 to 15 degrees. With this taper, the surfaces 72, 32 coact to effect a fluid seal.

The seal 40 of this invention is easily inserted onto the fitting 14 hereof by slipping the seal 40 onto the fitting 14 and then rotating the seal 40 by about a quarter to a half turn. This is done with the fingers and no special tools are required. The seal can be easily removed by reversing the procedure and bending off the seal. The seals 40 are relatively low cost items, and can be easily molded using conventional techniques. Thus, these seals 40 can be made disposable, thus saving the time, cost and effort required in cleansing the seal after each use of the endoscope. As observed previously, the fitting 14 also accommodates a syringe, gas fitting, or other luer lock type device without requiring any special tools or additional fittings, thus making the endoscope significantly more convenient than otherwise.

While the invention has been described in detail above with respect to a preferred embodiment, it should be recognized that the invention is not limited to that embodiment, and that many modifications and variations thereof would present themselves to those of skill in the art without departure from the scope and spirit of this invention, as defined in the appended claims.

I claim

1. A biopsy seal for sealably covering a luer lock type fitting which fitting includes a tubular hollow stem and a pair of radial retaining flanges at a free end thereof, the seal permitting insertion of an elongated instrument of generally circular cross-section therethrough and through the stem of said fitting, the biopsy seal being formed of a generally tubular body of an elastomeric material and comprising a proximal sealing portion, a distal seating portion, and a medial portion connecting said distal and proximal portions;

said proximal sealing portion including an outer transverse wall having a central opening therein and a transverse sealing plate disposed within said body behind said outer transverse wall, said wall and plate defining a generally disc-shaped cavity therebetween, and said transverse plate having a slit across it and being yieldable to open for insertion of said elongated instrument through said opening and said slit in the direction toward the distal end of the biopsy seal and remaining closed when said instrument is not inserted therethrough, said transverse wall sealing against the side of the circular cross-section instrument when the same is inserted through said opening;

said distal seating portion including a cylindrical passage for receiving the stem of said fitting; and said medial portion including means for engaging the radial retaining flanges of said fitting.

2. A biopsy seal according to claim 1 wherein said outer transverse wall has a concave outer surface.

3. A biopsy seal according to claim 1 wherein said proximal portion has a barrel-shaped circumferential wall to facilitate placement and removal of the seal.

4. A biopsy seal according to claim 1 further comprising a fill of a suitable lubricant disposed in said cavity.

5. A biopsy seal according to claim 1 wherein said opening in said outer transverse wall is constructed to seal with instruments having a cross-section diameter of 2.2 mm to 3.8 mm.

6. A biopsy seal according to claim 1 wherein said elastomer is a soft biocompatible synthetic polymer.

7. A biopsy seal according to claim 1 wherein said transverse plate includes one-way hinging means joining said plate to a side wall of the proximal portion of the tubular body, permitting said slit to open when said instrument is inserted through said opening and is pushed distally against said transverse sealing plate, but maintaining said slit tightly shut under pressure from the distal side of said transverse sealing plate.

8. A biopsy seal according to claim 7, wherein said hinging means includes a hinge portion joining said plate and said side wall and offset towards the proximal side of said plate.

9. A biopsy seal for sealably covering a luer lock type fitting which fitting includes a tubular hollow stem and a pair of radial retaining flanges at a free end thereof, the seal permitting insertion of an elongated instrument therethrough and through the stem of the fitting, the biopsy seal being formed of a generally tubular body of an elastomeric material and comprising a proximal sealing portion, a distal seating portion, and a medial portion connecting said distal and proximal portions;

said proximal sealing portion including an outer tubular wall and a transverse sealing plate disposed within said body and having a slit across it, the plate being yieldable to open for insertion of said elongated instrument therethrough, said transverse sealing plate having a hinge portion connecting said plate to said side wall, said hinge portion being offset towards the proximal end of the transverse sealing plate so that pressure at the proximal side of said plate urges said slit open but pressure at the distal side thereof urges said slit tightly shut;

said distal seating portion including a cylindrical passage for receiving the stem of said fitting; and said medial portion including means for engaging the radial retaining flanges of said fitting.

10. A biopsy seal according to claim 9 wherein said hinge portion and said transverse sealing plate define an undercut portion on the distal side of the plate.

11. A biopsy seal according to claim 9 wherein said hinge portion extends slopingly from a radial edge of said plate proximally to said side wall.

12. A biopsy seal according to claim 9, further comprising means disposed proximally of said transverse sealing plate defining a circular seal for sealing against said elongated instrument.

13. A sealable fitting for an external end of a biopsy channel, the fitting comprising a generally cylindrical metal plug having threads for engaging mating threads of said biopsy channel external end and having an axial aperture therethrough; a hollow luer stem disposed axially on said plug on a proximal side thereof and having a pair of oppositely disposed radial flanges at the proximal end of said stem; and a retaining ring formed on the proximal side of said plug surrounding said stem, the retaining ring having a flat transverse surface and a frustoconic tapered surface facing said stem.

14. A sealable fitting according to claim 13 wherein said frustoconic surface is tapered with respect to the center axis at an angle of about 12 to 15 degrees.

15. A sealable fitting according to claim 13 wherein said fitting is unitarily formed of a suitable biocompatible metal.

16. A sealable fitting according to claim 15 wherein said metal is stainless steel.

17. A biopsy seal for sealably covering a luer-lock type fitting which fitting includes a tubular hollow stem and a pair of radial retaining flanges at a free end thereof, the fitting also including a retaining ring surrounding the stem and having a flat transverse sealing surface and a tapered frustoconic surface facing the stem; the biopsy seal being formed of a generally tubular body of an elastomeric material and comprising a proximal sealing portion, a distal seating portion, and a medial portion connecting the distal and proximal portions;

said proximal sealing portion including means permitting insertion of an elongated instrument therethrough and thence through said hollow stem of said fitting, but resisting release of fluids out of the proximal end of said seal;

said distal seating portion including a cylindrical passage for receiving the stem of said fitting, a transverse flange for sealably engaging the flat transverse sealing surface of said retaining ring, and an axially protruding annulus extending distally of said flange and having a frustoconic tapered outer surface mating with the stem-facing surface of the sealing ring of said fitting.

18. A biopsy seal according to claim 17 in which said frustoconic outer surface has a taper with respect to the center axis of about 12 to 15 degrees.

19. A biopsy seal according to claim 17 wherein said cylindrical passage has a shoulder at a proximal end thereof for engaging beneath the radial retaining flanges of said fitting.

20. A biopsy seal according to claim 17 wherein said medial portion is thinner walled than said proximal and said distal portions.

* * * * *